(12) United States Patent
Riedel (10) Patent No.: US 10,207,058 B2
(45) Date of Patent: Feb. 19, 2019

(54) PEN-TYPE DRUG INJECTION DEVICE WITH PARTICULAR DOSE SCALE AND DOSE DISPLAY WINDOW COMPRISING OPTICAL FILTER FOR UNAMBIGUOUS DISPLAY OF SET DOSE VALUE

(71) Applicant: SANOFI-AVENTIS DEUTSCHLAND GMBH, Frankfurt am Main (DE)

(72) Inventor: Stephan Riedel, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/124,946

(22) PCT Filed: Mar. 23, 2015

(86) PCT No.: PCT/EP2015/056035
§ 371 (c)(1),
(2) Date: Sep. 9, 2016

(87) PCT Pub. No.: WO2015/150127
PCT Pub. Date: Oct. 8, 2015

(65) Prior Publication Data
US 2017/0014577 A1  Jan. 19, 2017

(30) Foreign Application Priority Data
Mar. 31, 2014 (EP) ..................................... 14162564

(51) Int. Cl.
*A61M 5/31* (2006.01)
*A61M 5/315* (2006.01)
(Continued)

(52) U.S. Cl.
CPC .... *A61M 5/31535* (2013.01); *A61M 5/31551* (2013.01); *B42D 25/20* (2014.10);
(Continued)

(58) Field of Classification Search
CPC .......... A61M 5/31353; A61M 5/31551; A63F 2009/0613; A63F 2009/0615;
(Continued)

(56) References Cited

U.S. PATENT DOCUMENTS 3,001,503 A * 9/1961 Hezel ..................... G01D 13/12
116/285
3,969,830 A * 7/1976 Grasham ............ G07C 9/00055
380/54
(Continued)

FOREIGN PATENT DOCUMENTS

EP  2201973  6/2010
WO  WO-2010020311 A1 *  2/2010  ........ A61M 5/31551

OTHER PUBLICATIONS

International Preliminaly Report in International Application No. PCT/EP2015/056035, dated Oct. 4, 2016, 7 pages.
(Continued)

*Primary Examiner* — Charles A Fox
*Assistant Examiner* — Christopher E Veraa
(74) *Attorney, Agent, or Firm* — Fish & Richardson P.C.

(57) ABSTRACT

The present invention relates to a pen-type drug injection device, comprising a dose scale drum (22) and having a housing (12) with a window (14) covered by an optical filter (50), the dose scale drum being displaceable axially relative to the housing during dose setting such that the dose value set can be read through the window while at least a portion of the dose scale drum protrudes from the housing. The dose values (42) are printed on an information surface (40) of the drum as an illegible pattern (48) together with a coding pattern (44), wherein the dose values (42) and the coding pattern (44) are designed such that light (52) reflected by or emanating from the illegible pattern (48) interacts with the optical filter (50) in such a way that the dose values (42) are exclusively recognizable through the optical filter (50) but
(Continued)

not on the part of the dose scale drum protruding from the housing. The optical filter can be a color filter or a polarization filter in order to achieve the desired effect. In this way confusion of the actually set dose value and dose values which would otherwise be visible on the part of the dose scale drum protruding from the housing can be avoided during dose setting.

20 Claims, 3 Drawing Sheets

(51) Int. Cl.
*G02B 5/20* (2006.01)
*B42D 25/36* (2014.01)
*B42D 25/351* (2014.01)
*B42D 25/20* (2014.01)
*G07D 7/128* (2016.01)
*G09F 3/02* (2006.01)

(52) U.S. Cl.
CPC ........... B42D 25/351 (2014.10); B42D 25/36 (2014.10); G02B 5/20 (2013.01); *A61M 2005/3126* (2013.01); *A61M 2205/583* (2013.01); *A61M 2205/586* (2013.01); *A61M 2205/587* (2013.01); *A61M 2205/6063* (2013.01); *G07D 7/128* (2013.01); *G09F 2003/0213* (2013.01)

(58) Field of Classification Search
CPC .... A63F 2009/01616; A63F 2009/0618; A63F 2009/0619; A63F 9/0613; B44F 1/10; B42D 25/20; B42D 25/351; B42D 25/36; G02B 5/20; G07D 7/128; G09F 2003/0213

See application file for complete search history.

(56) References Cited

U.S. PATENT DOCUMENTS

| | | | |
|---|---|---|---|
| 4,824,144 A | 4/1989 | Tasma | |
| 5,338,310 A * | 8/1994 | Lewandowski | A61M 5/3243 |
| | | | 604/110 |
| 5,401,032 A * | 3/1995 | Barnhart | A63F 1/02 |
| | | | 273/293 |
| 8,016,156 B2 * | 9/2011 | Sawin | B65D 77/0453 |
| | | | 221/155 |
| 2010/0025476 A1 | 2/2010 | Widzinski et al. | |
| 2010/0274198 A1 | 10/2010 | Bechtold | |

OTHER PUBLICATIONS

International Search Report and Written Opinion in International Application No. PCT/EP2015/056035, dated Sep. 3, 2015, 11 pages.
Jacobson, "How to use colored filters to send secret messages", Apr. 23, 2012, Retrieved from the Internet: URL: http://www.education.com/science-fair/article/colored-filters-send-secret-messages/.

* cited by examiner

PEN-TYPE DRUG INJECTION DEVICE WITH PARTICULAR DOSE SCALE AND DOSE DISPLAY WINDOW COMPRISING OPTICAL FILTER FOR UNAMBIGUOUS DISPLAY OF SET DOSE VALUE

CROSS-REFERENCE TO RELATED APPLICATIONS

This application is a U.S. national stage application under 35 USC § 371 of International Application No. PCT/EP2015/056035, filed on Mar. 23, 2015, which claims priority to European Patent Application No. 14162564.0 filed on Mar. 31, 2014, the entire contents of which are incorporated herein by reference.

The present invention relates to a display arrangement of or for a drug delivery device and to a respective drug delivery device. In particular, the invention relates to an injection device such like a pen-type injector inter alia comprising a housing with a display member displaceable from a retracted position into an extended position, in which a portion thereof protrudes from the housing.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

In particular with users or patients being physically or visually impaired correct handling of the device is sometimes cumbersome. Typically, such devices comprise and provide visual or readable indicators or display elements in order to inform the user or patient of the actual status and configuration of the device. Such information should be clearly and unambiguously legible, even for visually impaired persons.

Document WO 2013/050461 A1 discloses a display arrangement for a drug delivery device comprising a first display member with numerous surface portions having at least two different but interrelated appearances and being alternately arranged along a first direction. The display arrangement further comprises a second display member with a light modulating structure to modulate visible light emanating from the first display member. First and second display members are moveably disposed relative to each other to simultaneously reveal and/or to conceal at least two surface portions of interrelated appearance.

With drug delivery devices such as for instance described in EP 1 603 611 B1 a dose dial sleeve can be rotated with respect to a housing until a desired dose value is visible through a window of said housing. Upon selecting of a dose the dose dial sleeve is rotated and extends from a proximal end of the housing since it is threadedly engaged with the housing via a helical thread. It may then happen, that various symbols or indicia provided on the dose dial sleeve also extend from a proximal end of the housing. A user of the device may get confused by multiple indicia appearing in the window as well as beyond a proximal end of the housing. It may arise, that the user misinterprets the respective symbols or numbers that appear beyond the proximal end of the housing and that the user consequently selects or dials an inappropriate dose.

OBJECTS OF THE INVENTION

Certain aspects of the present invention relate to an improved display arrangement adapted to display different configurations or device states in an intuitive and unambiguous way. The improvements can be obtained by minimum modifications to the existing display arrangements and/or drug delivery devices. The display arrangement should be robust, reliable, intuitive as well as cost efficient in terms of manufacturing and assembly. Furthermore, the display arrangement should be easily and intuitively legible and should visually provide information with sufficient and large contrast.

SUMMARY OF THE INVENTION

In a first aspect the invention relates to a display arrangement for a drug delivery device. The display arrangement comprises a housing having a window which is covered by an optical filter. Said housing may coincide with the housing of the drug delivery device or may be configured as a portion thereof. The display arrangement further comprises a display member displaceable relative to the housing between a retracted position and an extended position. The display member overlaps with the window so that the display member is legible through the optical filter that covers the housing's window. When in extended position at least a portion of the display member, typically a proximal portion thereof protrudes from the housing. Even when in the extended position at least another portion of the display member still overlaps with the housing's window so that a respective indicia coinciding with the actual position of the display member relative to the housing is legible through or in the window.

The display member further comprises an information surface with an illegible pattern. The information surface may cover the complete outer surface of the display member or only selected portions thereof. The illegible pattern comprises an information content and a coding pattern. Typically, information content and coding pattern mutually overlap on the information surface of the display member. While the information content typically comprises numerous indicia, symbols or numbers that are configured to successively appear in the window to display the size of a dose actually set or dialed, the coding pattern is configured to make the information content substantially illegible, so that the information surface as it is provided on the outer surface of the display member becomes illegible in such a way that it cannot be analyzed or processed by a user without the aid of the optical filter.

Moreover, at least one of the information content and the coding pattern is designed such that light reflected by or emanating from the illegible pattern interacts with the filter in such a way that the information content is exclusively recognizable through the filter. Hence, light emanating from the information content and emanating from the coding pattern interacts with the optical filter in such a way, that the optical contribution of the coding pattern is hidden or blinded out so while the light emanating from the information content may propagate through the optical filter so as to provide legible information content to a user exclusively in the region of the window.

By having an illegible pattern on the information surface of the display member, a respective portion of the display member extending from e.g. a proximal end of the housing is no longer be legible or readable by a user. A relevant information content representing an actual state or configuration of the drug delivery device is exclusively and unambiguously legible in or through the window.

Compared to existing display arrangements for drug delivery devices the present invention only requires to provide a suitable optical filter in the aperture of the window and to modify the visual appearance of the information surface in a well-defined way so that a relevant information content, e.g. a sequence of dose size indicating numbers is only visible through the window but not at other portions or regions of the housing of the display arrangement or of the respective drug delivery device. Modification of the window by placing an optical filter across the window and by superimposing or adding a coding pattern to the information content of the display member's information surface is a rather cost efficient and effective means to modify and to improve the display arrangement.

The coding pattern may comprise an irregularly distributed spatial structure being configured to render and to make the information content illegible. The coding pattern may comprise artificial two-dimensional visual structures. It may for instance comprise a predefined homogeneous or inhomogeneous texture. It may comprise artificial and multiple overlaying text fragments. The coding pattern may be selectively provided only in the vicinity and circumference of single or multiple bits of the information content. It may also cover the entire outer surface of the display member. When the information content comprises a sequence of numbers or symbols the coding pattern may be provided only locally around respective numbers or symbols. In other embodiments the coding pattern completely covers the information surface so that it is even impossible to localize a portion on the information surface that carries an information content or which reflects an empty space between consecutive numbers or symbols.

According to a further embodiment the optical filter is optically transmissive for light reflected by or emanating from the coding pattern. Given that the coding pattern is distinguishable from a plain background of the information content and that light incident on the coding pattern is modulated, either in regard of its polarization and/or spectral range when reflected by the coding pattern, the optical filter is typically designed and configured in accordance with the light modulating characteristics of the coding pattern so that light reflected or emanating from a plain background of the information surface is manipulated and modified by the optical filter in substantially the same way as the light incident on the coding pattern is modulated or modified by the coding pattern.

By making use of an optical filter being transmissive for light reflected by or emanating from the coding pattern a contrast between the coding pattern and the plain background of the information surface can be blinded out or suppressed. By means of the optical filter the light modulating characteristics of the coding pattern can be compensated or effectively counteracted so that the information content exclusively reveals after transmission through the optical filter.

According to another embodiment the filter is optically absorptive for light reflected by or emanating from the coding pattern. In this embodiment light reflected or emanating from the coding pattern cannot transmit through the optical filter but may be absorbed or reflected by the filter. Hence, any visual contribution of the coding pattern to the overall impression of the information surface and the display member can be effectively suppressed. As a consequence only light reflected by or emanating from the information content is transmitted through the optical filter and is therefore exclusively recognizable through the optical filter.

According to a further embodiment the optical filter is optically transmissive for light reflected by or emanating from the information content. The transmissivity of the optical filter may not equal 100%. It may be sufficient, when the transmissivity of the optical filter for light reflected by or emanating from the information content is larger than 20% so that light reflected by or emanating from the information content is sufficiently detectable from outside the housing to allow a sufficient degree of legibility. Hence, the light reflected by or emanating from the information content may be attenuated by the optical filter only to a certain and/or predefined degree so that enough light representing the information content can pass through the optical filter.

In a further embodiment the information content comprises numerous symbols overlapping with the coding pattern or being embedded in the coding pattern. The information content may include and may comprise a sequence of indicia, i.e. a sequence of number or symbols that are configured to display the size of a dose of a drug or medicament actually set by the drug delivery device. The symbols or indicia of the information content may be arranged in an order that corresponds to the displacement of the display member relative to the housing. If the display member is for instance engaged with the housing via a helical thread, the symbols or indicia of the information content are arranged in a corresponding helical way so that a longitudinal or axial displacement of the display member relative to the housing leads to an incrementing or decrementing sequence of indicia that show up in the window.

The information content and the coding pattern may be provided on substantially overlapping layers, that may be sequentially or simultaneously printed on the information surface. It is even conceivable, that information content and coding pattern are printed on a substantially planar-shaped label that is wrappable and/or attachable around the outer circumference of the display member. It is particularly conceivable that the information content is printed on top of the coding pattern completely or at least partially covering the entire information surface of the display member. It may be due to the spatial structure of the coding pattern, that the information content is non-recognizable since the visual contrast of the coding pattern and the visual contrast of the information content are substantially equal. Here, the human eye may not be able to selectively identify the information content which is printed or located on top of the coding pattern.

Instead of an overlapping configuration it is also conceivable, that the information content is embedded in the coding pattern in a non-overlapping way. Hence, the coding pattern comprises void spaces with a geometry and spatial or two-dimensional structure that matches with the geometry and structure of the symbols or indicia of the information content.

According to a further embodiment the coding pattern and the information content comprise different colors. In this way, the optical reflectance of the coding pattern may differ from the optical reflectance of the information content. By making use of an appropriate optical filter, the light reflected by the information content can be exclusively visualized while the light reflected by the coding pattern is effectively suppressed, either by way of absorption or by way of reducing the contrast of the optical pattern reflected from the coding pattern with regard to the light reflected by or emanating from a plain background.

Making use of different colors for the coding pattern and the information content is a rather effective and easy implementable means to conceal the information content on the information surface and to make the information surface generically illegible.

In a further embodiment the average brightness or saturation of the coding pattern is equal to or substantially equivalent to the brightness or saturation of the information content. Since the coding pattern provides and comprises a small-sized irregular spatial distribution of picture elements or pixels the coding pattern comprises a well-defined average brightness or saturation. By adapting the brightness or saturation of the information content to the coding pattern's brightness or saturation the information content can be effectively concealed by the coding pattern either surrounding or overlapping with the information content.

For instance, the coding pattern may comprise a predefined degree of coverage of the plain background on the information surface. The degree of coverage comprises an average brightness or saturation. By selecting the brightness or saturation of the information content, e.g. by making use of a color of the information content having an equivalent brightness or saturation the information content can be effectively concealed in the surrounding of the coding pattern.

According to another embodiment the optical filter comprises a color filter matching with the color of one of the coding pattern and information content. The coding pattern typically comprises a single color. Also the information content may comprise a single but different color. Making use of a color filter matching for instance with the color of the coding pattern the contrast of the optical pattern reflected or emanating from the coding pattern can be effectively reduced so that the coding pattern itself is no longer visible when viewed through the optical filter. Since the optical filter is transmissive for light reflected by or emanating from the information content it is only and exclusively the information content which becomes readable or legible from outside the window and from outside the optical filter.

In an embodiment wherein the color filter matches with the color of the information content the color filter is preferably adapted and configured to absorb the light reflected by or emanating from the coding pattern and/or from the plain background of the information surface.

In still another embodiment the coding pattern and the information content provided on the information surface as the illegible pattern have different polarizing effects on incident light. Hence, one of coding pattern and information content are configured to reflect incident light at a predefined polarization. Consequently and according to a further embodiment the optical filter then comprises a polarization filter configured and adapted to the polarizing reflecting behavior of one of coding pattern and information content. In this way the coding pattern can be effectively filtered, absorbed or reflected by the optical filter so that only light reflected by or emanating from the information content is recognizable through the optical filter.

According to a further embodiment the housing of the display arrangement comprises a longitudinal shape and extends in an axial direction. Furthermore, the display member comprises a dose dial sleeve that is co-aligned with the housing and which is threadedly engaged with the housing, e.g. by way of a helical thread. Dialing, hence rotating the dose dial sleeve relative to the housing then leads to a longitudinal displacement of the dose dial sleeve relative to the housing in longitudinal direction, in particular in distal or proximal direction. The display arrangement may be configured to comprise a separate housing so that the display arrangement together with its housing may be attachable or insertable to or into a drug delivery device. In alternative embodiments the housing of the display arrangement coincides with the housing of the drug delivery device or a portion thereof. Hence, display arrangement and drug delivery device share a common housing.

In still another embodiment the display member is operably engageable with a dose dial arranged at a proximal end of the display member for inducing a screw-like and proximally-directed displacement of the display member relative to the housing. Between dose dial and display member there is typically provided a clutch mechanism so that the rotational engagement of dose dial and display member can be deactivated during does dispensing, i.e. when the display member returns from the extended position towards into the initial or retracted position. When in an initial or retracted position the clutch or ratchet mechanism between the dose dial and the display member is configured to establish a rotational coupling between display member and dose dial, so that a dose incrementing and/or a dose decrementing rotation of the dose dial unalterably transfers to a respective helical rotation of the display member.

According to another aspect the invention also relates to a drug delivery device for dispensing a dose of a medicament. The device comprises a drive mechanism with a piston rod to operably engage with a piston of a cartridge containing the medicament. The drug delivery device further comprises a display arrangement as described above and further comprises a housing in which the drive mechanism and the display mechanism's dose display members are arranged. As already described the display member may be displaceably arranged in the housing of the display arrangement or in a housing of the respective drug delivery device so that it is displaceable between a retracted or initial configuration, in which the display member in its entirety is located inside the housing and an extended position, in which at least a proximal portion of the display member extends from a proximal end of the housing.

Typically, the drive mechanism and the drug delivery device also comprises a dose button, which may be also provided at a proximal end of the display member. By depressing the dose button the dose member together with a drive sleeve of the drive mechanism can be urged into the housing and in distal direction, under the effect of a user-induced actuation. This distally-directed displacement of the drive sleeve is transferable into a respective distally-directed displacement of the drive mechanism's piston rod in order to displace the cartridge's piston in distal direction for expelling a dose of a liquid medicament from the cartridge.

According to another embodiment the drug delivery device comprises a cartridge holder which is connectable to a distal portion of the housing and which is configured to receive the cartridge that is filled with the medicament. Cartridge holder and distal portion of the housing, hence the body of the drug delivery device may be non-releasably interconnected, in particular when the drug delivery device is designed as a disposable device. In other embodiments cartridge holder and housing of the drug delivery device can be releasably connected so as to allow replacement of an empty cartridge. In still another embodiment the drug delivery device comprises a cartridge containing the medicament, wherein the cartridge is arranged inside the cartridge holder or inside the housing of the drug delivery device.

In the present context, the distal direction points in the direction of the dispensing and of the device, where, preferably a needle assembly is provided having a double-tipped injection needle that is to be inserted into biological tissue or into the skin of a patient for delivery of the medicament. The proximal end or proximal direction denotes the end of the device or a component thereof, which is furthest away from the dispensing end.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39),
wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE DRAWINGS

In the following various embodiments of the present application will be explained in detail by making reference to the drawings, in which.

DETAILED DESCRIPTION

Figure 1:
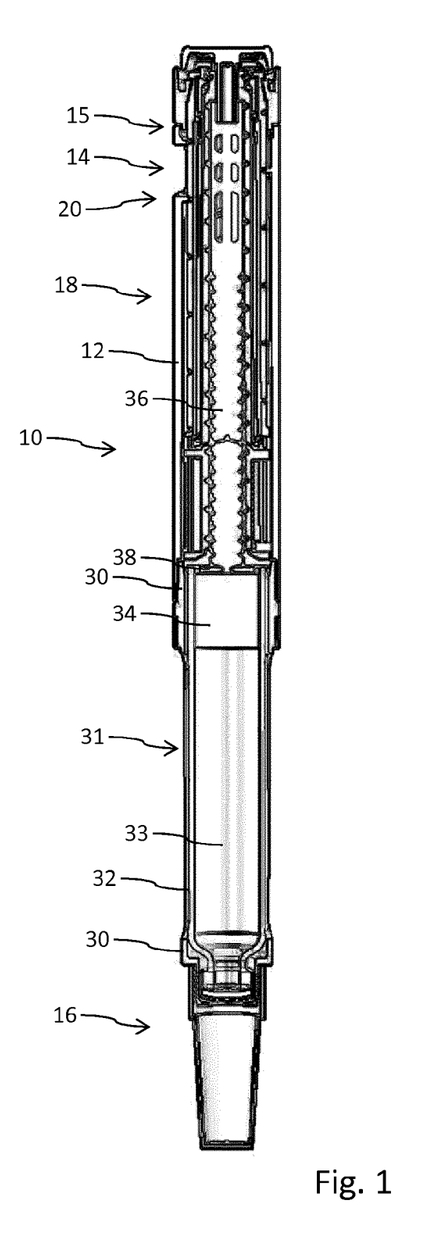
FIG. 1 schematically shows a longitudinal cross-section through a drug delivery device with the display member in an initial retracted position.
Figure 2:
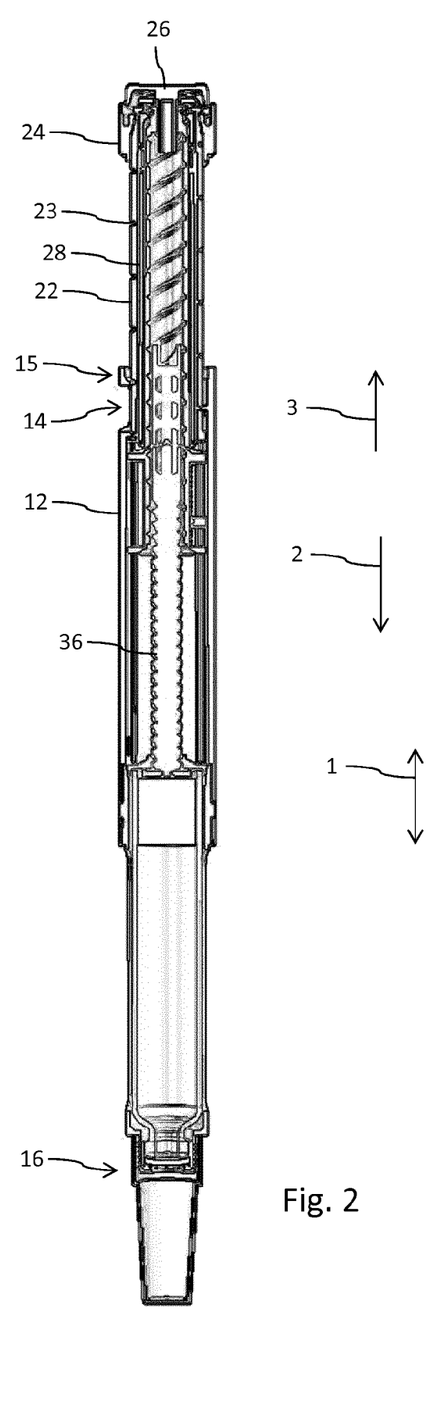
FIG. 2 shows the device according to FIG. 1 with the display member in a longitudinally extended configuration.

In FIGS. 1 and 2 a drug delivery device 10 is illustrated in longitudinal cross-section in two different configurations. The drug delivery device 10 is configured as a user-operated injection device. The drug delivery device comprises a longitudinal geometry. Hence, the housing 12 of the drug delivery device 10 extends in a longitudinal or axial direction 1. In distal direction 2 the drug delivery device 10 features a distal end 16 that serves as a dispensing end. The distal end 16 is engageable with an injection needle or with a respective needle assembly, which is not particularly illustrated here.

As shown in FIGS. 1 and 2 the distal end 16 of the drug delivery device 10 is covered by a protective cap 17. The housing 12 is located at a proximal end 15 of the drug delivery device 10. The housing 12 may therefore constitute and form the proximal end 15 it may constitute a proximally located body of the drug delivery device 10. The proximal housing 12 is of substantially tubular or cylindrical shape. Near its proximal end 15 it comprises a window 14 which is provided and formed by an aperture in a sidewall portion of the housing 12. In distal direction 2 the housing 12 is interconnected with a cartridge holder 30. The cartridge holder 30 is configured to receive and to accommodate a cartridge 32 that contains a liquid medicament 33.

In proximal direction 3 the cartridge 32 is sealed by a piston 34 which is displaceably arranged inside the cartridge 32, hence inside a barrel, which is typically a vitreous barrel. The cartridge holder 30 also comprises at least one inspection window 31 through which the content of the cartridge 32 can be visually inspected.

In the initial configuration as illustrated in FIG. 1 the piston 34 of the cartridge 32 is effectively axial abutment or in direct contact with a pressure piece 38 that is located at a distal end of a piston rod 36. The piston rod 36 is axially guided inside the housing 12. By means of a drive mechanism 18, which is also accommodated in the housing 12 the piston rod 36 is displaceable in distal direction 2 in order to exert distally-directed pressure onto the piston 34. As a consequence, the piston 34 is urged by the piston rod 36 in distal direction 2 so as to expel a predefined amount of the medicament 33, hence a dose of the medicament 33 from the cartridge 32.

The piston rod 36 may be rotatably fixed and axially guided in and relative to the housing 12. There are also embodiments, in which the piston rod 36 may be threadedly engaged with the housing 12 so that a rotation of the piston rod 36 leads to a distally-directed displacement of the piston rod 36 relative to the housing 12 and hence relative to the body of the cartridge 32.

The drive mechanism 18 further comprises a drive sleeve 28 threadedly engaged with the piston rod 36. In alternative embodiments the drive sleeve 28 may also be selectively and releasably rotatably or slidably engageable with the piston rod 36. The drive sleeve 28 is further coupled with a dose dial 24 located at a proximal end of the drive sleeve 28 or of a display member 22. In addition, the drive mechanism 18 comprises a dose button 26 located at the proximal end 15 of the drug delivery device 10.

The display member 22, the drive sleeve 28 as well as the piston rod 36 may be arranged in a convoluted or nested way as illustrated in FIG. 1 when the drug delivery device 10 and its drive mechanism 18 are in an initial configuration. The drive sleeve 28 is located and arranged inside the hollow and sleeve-shaped display member 22. The display member 22 in its retracted and initial configuration as shown in FIG. 1 is almost completely located inside the hollow and tubular-shaped housing 12. Inside the drive sleeve 28 there is located the piston rod 36.

The drive mechanism 18, which is described in more detail for instance in document EP 1 603 611 B1 comprises at least one clutch not further illustrated here. By means of a clutch the dose dial 24 is selectively engageable and disengageable with and from the drive sleeve 28 and/or the display member 22. For selecting or setting of a dose a user may just rotate the dose dial 24 relative to the housing 12. Due to a rotational coupling between the dose dial 24, the drive sleeve 28 and the display member 22 and due to the engagement of the display member 22 with the housing 12 by means of a helical thread 23 the display member 22 experiences a helical motion according to which the display member 22 together with the drive sleeve 28, dose dial 24 and dose button 26 separates and extends from the proximal end 15 of the housing 12 in proximal direction 3. For injecting and for dispensing of a dose a user may depress the dose button 26 thereby releasing a clutch between the dose dial 24 and at least one of display member 22 and drive sleeve 28. A user-driven and distally-directed displacement of the dose button 26 returns the display member 22 back into its initial and retracted configuration as shown in FIG. 1 while the piston rod 36 advances in distal direction 2 for dispensing of a dose of the medicament 33.

Figure 3:
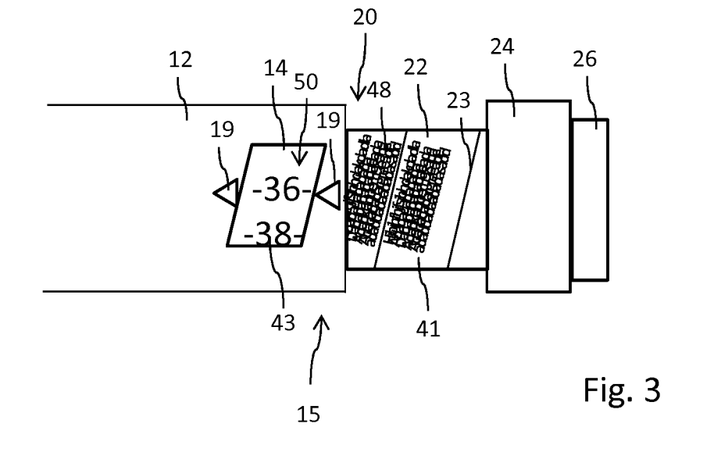
FIG. 3 represents a schematic view of the proximal end of the housing with the display member in an extended configuration.

In FIG. 3 a schematic illustration of the proximal end 15 of the housing 12 is provided. As indicated there, the sidewall of the housing 12 comprises an aperture or through opening that provides a window 14. Through the window 14 a portion of the display member 18 is discernible and visible. In order to identify a size of a dose actually set the housing 12 comprises at least one indicator 19 at a proximal or distal edge of the window 14. The indicia 43 or numbers located in line with the indicator 19 or indicators represents the size of a dose actually set during a dose setting procedure. In the extended position at least a proximal portion of the display member 22 extends from the proximal end 15 of the housing 12. With drug delivery devices 10 according to the prior art respective indicia or numbers indicating the size of a dose may become discernible or legible as respective indicia become visible beyond the proximal end 15 of the housing 12.

Figure 4:
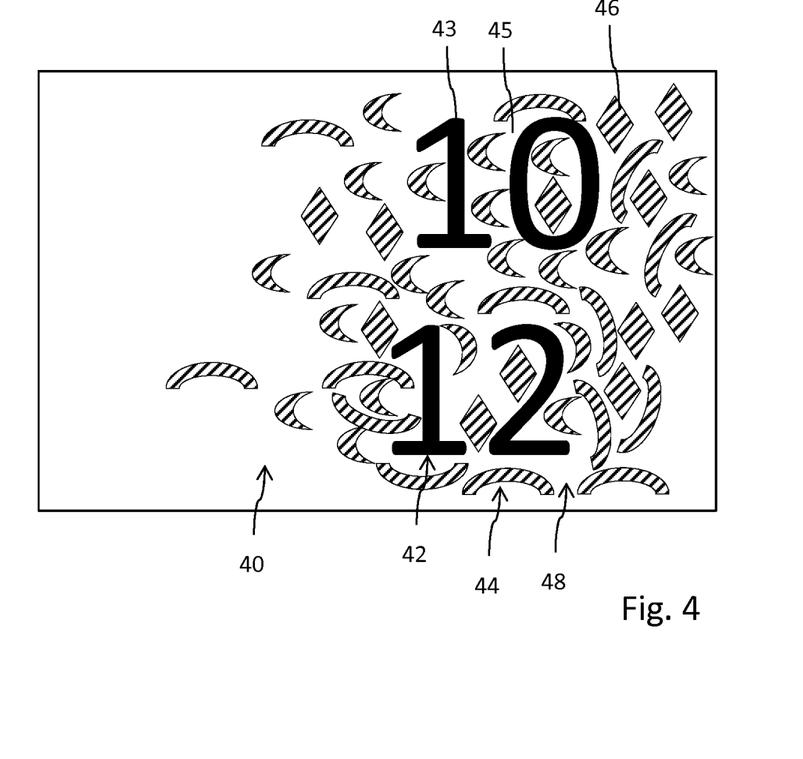
FIG. 4 shows an enlarged schematic illustration of the illegible pattern consisting of information content and coding pattern, FIG. 5 schematically illustrates the interaction of incident and reflected light with the filter according to a first embodiment, and FIG. 6 schematically illustrates interaction of incident and reflected light with the optical filter according to another embodiment.

In order to prevent misinterpretation of the display arrangement 20 as illustrated in FIG. 3, the display member 22 comprises an information surface 40 that comprises an illegible pattern 48 as it is schematically illustrated in FIG. 4. The illegible pattern typically covers the complete information content 42 provided on the display member's 22 information surface 40. The illegible pattern 48 comprises an information content 42, such like a sequence of indicia or numbers to represent and to indicate the size of a dose. The illegible pattern further comprises a coding pattern 44 by way of which the information content 42 becomes illegible. In other words, the coding pattern 44 serves to hide or to conceal the legible information content 42 of the display member 22.

In the sketch according to FIG. 4 the illegible pattern 48 is represented in a rather unrealistic way since the information content 42, presently represented by consecutive numbers is actually recognizable and legible for illustration purpose only. In a real embodiment the information content 42 is not recognizable or legible by a user without the help of an optical filter 50, which covers the window 14 of the housing 12.

Typically, the illegible pattern 48 covers the complete outer circumference of the sleeve-shaped display member 22. In alternative embodiments it is conceivable that the illegible pattern 48 only covers or coincides with the position and geometric expansion of the symbols or indicia 43 of the information content 42.

In FIG. 4, various coding segments 46 are schematically illustrated. Just for illustration purpose and in order to distinguish the coding pattern 44 from the information content 42 the information content 42 is illustrated in bold face whereas the coding pattern 44 formed by a spatial distribution of various coding segments 46 is illustrated as dashed structures.

The optical filter 50 completely covering the window 14 matches and corresponds with the reflective optical behavior of the illegible pattern 48, in particular with its information content 42 and/or with its coding pattern 44. In general, the light reflected by or emanating from the illegible pattern 48, hence the superposition of light reflected from the information content 42 and light reflected from the coding pattern 44 is such, that after transmission through the optical filter 50 only a light pattern emanating from or reflected by the information content 42 remains visible to a user.

Figure 5:
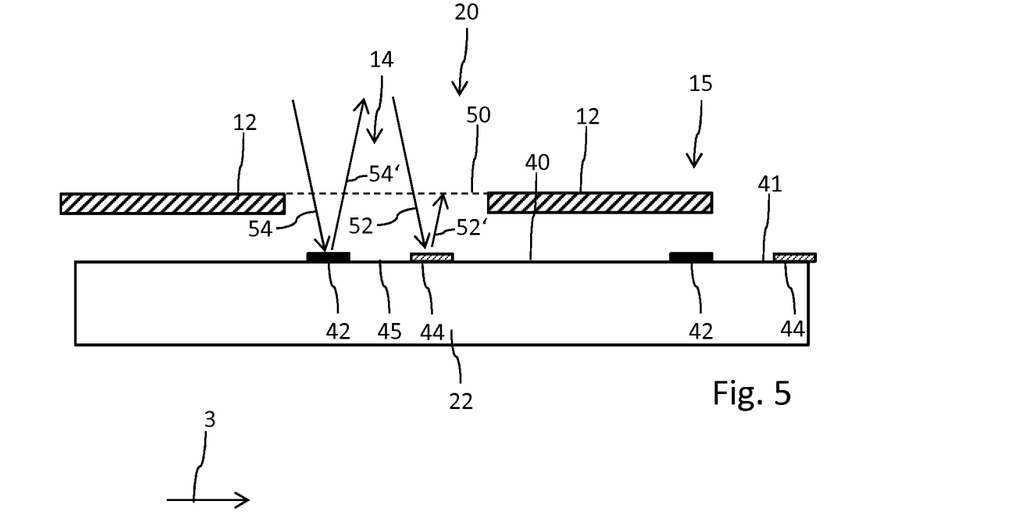

In the sketch of FIG. 5 incident light 54, 52 e.g. of a rather broad spectral range is transmitted through the optical filter 50 and is incident on the information surface 40 of the display member 22. Light 54' reflected by the information content 42 is transmitted through the optical filter 50 while light reflected or otherwise emanating from the coding pattern as reflected light 52' is absorbed or reflected by the optical filter 50 so that this light portion 52' is hindered from contributing to the visual appearance of the information surface 40 outside the housing 12. The eye of a user may therefore only receive a pattern of light 54' that is reflected or emanated from the information content 42. In this way, only those indicia 43 of the information content 42 that are located underneath the optical filter 50 and which coincide with the window are legible for a user from outside the housing 12.

A proximal portion 41 of the information surface 40 of the display member 22 extending outside the housing in proximal direction 3 is illegible since there only the complete but non-filtered illegible pattern 48 is visible.

Figure 6:
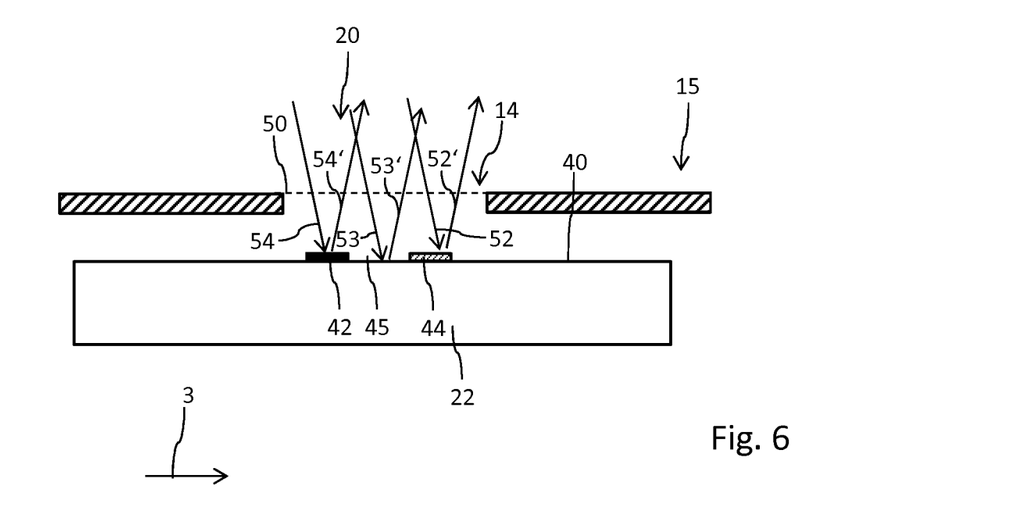

In FIG. 6 an alternative embodiment is shown, wherein the optical filter 50 is transmissive for light 54' reflected by or emanating from the information content 42 as well as for light 52' reflected by or emanating from the coding pattern 44.

In FIG. 6 an incident light pattern consisting of or comprising light portions 52, 53, 54 is incident on the information surface 40 of the display member 22. The information content 42, hence the indicia 43 thereof distinguish from the coding pattern 44, hence from the coding segments 46 thereof by their reflecting properties.

For instance, the color of the coding pattern 44 distinguishes from the color of the information content 42. Hence, light 52' reflected or emanating from the coding pattern 44 comprises a spatial distribution that varies from the spatial distribution of the light 54' reflected by or emanating from the information content 42. In addition the information surface 40 comprises a spatial distribution of plain background portions 45 that are located between the coding segments 46 of the coding pattern 44 and the indicia 43 of the information content 42.

The plain background 45 may exhibit a rather neutral optical reflection behavior. Hence, the spectrum of light 53' reflected by or emanating from the plain background portions 45 may be substantially equal in regard to its spectral distribution or in regard to its polarization compared to the light 53 incident on the plain background portions 45. In this embodiment it is of particular benefit, when the optical filter 50 is configured as a color filter that has substantially the same color as the coding pattern 44. If for instance the coding pattern comprises a red color, light 52' reflected by the coding pattern 44 is substantially in the red wavelength range.

In addition, the optical filter 50 is then configured to by transmissive for the red spectral range, so that the light 52' reflected by the coding pattern 44 passes the optical filter 50 substantially unaltered. In addition, light 53' reflected by a plain background portion 45 remains substantially unaltered with regard to its spectral distribution after the reflection. But when passing through the optical filter 50 only the red spectral portion thereof will be transmitted through the optical filter.

As seen from outside, the light 52' reflected by the coding pattern 44 and the light 53' reflected by the plain background portion 45 exhibits substantially the same spectral range. As a consequence, the coding pattern 44 is blinded out and is effectively suppressed. The information content 42 which is of a color different to the color of the optical filter 50 and the color of the coding pattern 44 will then become discernible from outside the window 14. With a red color of the coding pattern 44 and with a red colored optical filter 50 it is beneficial when the information content is grey, e.g. at around 70% saturation.

When operating in a reflection geometry the optical filter 50 configured as a color filter already filters the incident light 52, 53, 54. In this way, the effect of erasing or suppressing the coding pattern 44 can be even enhanced.

Even though the coding pattern 44 and the information content 42 are illustrated to be located in one and the same layer on top of the information surface it is even conceivable, that the information surface 40 is covered with various overlapping layers, each of which representing at least a portion of the information content and/or at least a portion of the coding pattern. In various embodiments it is conceivable, that the coding pattern 44 is irregularly distributed across the entire information surface 40 and that the information content 42 is located or printed on top of the coding pattern. Especially when the average brightness or saturation of the coding pattern is substantially equal to the average brightness or saturation of the information content the information content is effectively concealed by the underlying coding pattern 44, so that the superposition of coding pattern 44 and information content 42 constitutes the illegible pattern 48, which is substantially illegible when located beyond the proximal end 15 of the housing 12.

LIST OF REFERENCE NUMBERS

1 axial direction
2 distal direction
3 proximal direction
10 drug delivery device
12 housing
14 window
15 proximal end
16 distal end
17 protective cap
18 drive mechanism
19 indicator
20 display arrangement
22 display member
23 helical thread
24 dose dial
26 dose button
28 drive sleeve
30 cartridge holder
31 inspection window
32 cartridge
33 medicament
34 piston
36 piston rod
38 pressure piece
40 information surface
41 proximal portion
42 information content
43 indicia
44 coding pattern
45 plain background portion
46 coding segment
48 illegible pattern
50 optical filter
52 light
53 light
54 light

The invention claimed is:

1. A display arrangement for a drug delivery device, the display arrangement comprising:
a housing defining a longitudinal shape, extending in an axial direction, and having a window covered by an optical filter, and
a sleeve-shaped display member configured to be displaced relative to the housing between a retracted position, in which the display member in its entirety is located inside the housing, and an extended position and overlapping with the window, wherein when in the extended position at least a proximal portion of the display member protrudes from a proximal end of the housing,
wherein the display member comprises an information surface with an illegible pattern,
wherein the illegible pattern comprises an information content and a coding pattern, wherein the information content comprises indicia, symbols, or numbers to display a size of a dose actually set or dialed, and
wherein the optical filter matches and corresponds with a reflective optical behavior of the illegible pattern, and wherein at least one of the information content and the coding pattern is arranged such that light reflected by or emanating from the illegible pattern interacts with the optical filter in such a way that the information content is recognizable through the optical filter.

2. The display arrangement according to claim 1, wherein the optical filter is optically transmissive for light reflected by or emanating from the coding pattern.

3. The display arrangement according to claim 1, wherein the optical filter is optically absorptive for light reflected by or emanating from the coding pattern.

4. The display arrangement according to claim 1, wherein the optical filter is optically transmissive for light reflected by or emanating from the information content.

5. The display arrangement according to claim 1, wherein the information content comprises numerous symbols overlapping with the coding pattern or embedded in the coding pattern.

6. The display arrangement according to claim 1, wherein the coding pattern and the information content comprise different colors.

7. The display arrangement according to claim 1, wherein an average brightness or saturation of the coding pattern is equal or substantially equivalent to an average brightness or saturation of the information content.

8. The display arrangement according to claim 1, wherein the optical filter comprises a color filter matching with a color of one of the coding pattern and information content.

9. The display arrangement according to claim 1, wherein the coding pattern and the information content have different polarizing effects on incident light.

10. The display arrangement according to claim 9, wherein the optical filter comprises a polarization filter.

11. The display arrangement according to claim 1, wherein the display member comprises a dose dial sleeve extending in the axial direction.

12. The display arrangement according to claim 11, wherein the display member is configured to engage with a dose dial arranged at a proximal end of the display member for inducing a screw-like and proximally directed displacement of the display member relative to the housing.

13. The display arrangement according to claim 1, wherein at least a portion of the illegible pattern is configured to protrude from the proximal end of the housing when the display member is in the extended position.

14. A drug delivery device for dispensing a dose of a medicament, the drug delivery device comprising:
- a drive mechanism comprising a piston rod configured to operably engage with a piston of a cartridge containing the medicament; and
- a display arrangement comprising:
  - a housing defining a longitudinal shape and extending in an axial direction and having a window covered by an optical filter, and
  - a sleeve-shaped display member configured to be displaced relative to the housing between a retracted position, in which the display member in its entirety is located inside the housing, and an extended position and overlapping with the window, wherein when in the extended position at least a proximal portion of the display member protrudes from a proximal end of the housing,
  - wherein the display member comprises an information surface with an illegible pattern, wherein the illegible pattern comprises an information content and a coding pattern, wherein the information content comprises one or more of incidence, symbols, and numbers to display a size of a dose actually set or dialed, and wherein the optical filter matches and corresponds with a reflective optical behavior of the illegible pattern and wherein at least one of the information content and the coding pattern is arranged such that light reflected by or emanating from the illegible pattern interacts with the optical filter in such a way that the information content is recognizable through the optical filter, and
  - wherein the drive mechanism and the display member are arranged in the housing.

15. The drug delivery device according to claim 14, further comprising a cartridge holder configured to be connected to a distal portion of the housing and to receive the cartridge.

16. The drug delivery device according to claim 15, further comprising a cartridge containing the medicament, the cartridge being arranged inside the cartridge holder, wherein the cartridge contains a pharmaceutically active compound.

17. The drug delivery device according to claim 14, further comprising a cartridge containing the medicament, the cartridge being arranged inside the housing.

18. The drug delivery device according to claim 14, wherein the cartridge contains a pharmaceutically active compound.

19. The drug delivery device according to claim 14, wherein at least a portion of the illegible pattern is configured to protrude from the proximal end of the housing when the display member is in the extended position.

20. A method comprising:
- rotating a dose dial of a drug delivery device relative to a housing of the drug delivery device to set a dose of a medicament to be expelled from the drug delivery device, the dose dial moving a portion of an illegible pattern underneath a window of the housing corresponding to the dose set by the dose dial, wherein the illegible pattern comprises an information content and a coding pattern and wherein the information content comprises at least one of indicia, symbols, and numbers to display a size of the dose actually set or dialed, wherein the window filters the coding pattern and reveals the information content to a user indicating the dose set by the dose dial, and wherein the dose dial moving the portion of the illegible pattern underneath the window comprises the dose dial exposing a proximal portion of the illegible pattern from a proximal end of the housing; and
- activing a drive assembly of the drug delivery device, the drive assembly expelling the dose of the medicament from the drug delivery device.

* * * * *

UNITED STATES PATENT AND TRADEMARK OFFICE
CERTIFICATE OF CORRECTION

PATENT NO. : 10,207,058 B2
APPLICATION NO. : 15/124946
DATED : February 19, 2019
INVENTOR(S) : Stephan Riedel Page 1 of 1

It is certified that error appears in the above-identified patent and that said Letters Patent is hereby corrected as shown below:

On the Title Page

In Column 2 (item (56), Other Publications), Line 1, delete "Preliminaly" and insert -- Preliminary --

In the Specification

In Column 1, Line 11, delete "371of" and insert -- 371 of --

In Column 1, Line 12, delete "2015,which" and insert -- 2015, which --

In the Claims

In Column 18, Line 34, Claim 20, delete "activing" and insert -- activating --

Signed and Sealed this
Twentieth Day of August, 2019

Andrei Iancu
*Director of the United States Patent and Trademark Office*